United States Patent
Heath (10) Patent No.: US 10,631,757 B2
(45) Date of Patent: Apr. 28, 2020

(54) SYSTEM AND METHOD FOR MONITORING PHYSIOLOGICAL FUNCTIONS

(75) Inventor: Chester Heath, Boca Raton, FL (US)

(73) Assignees: THE QUANTUM GROUP, INC., Lake Worth, FL (US); Noel J. Guillama, Wellington, FL (US)

( * ) Notice: Subject to any disclaimer, the term of this patent is extended or adjusted under 35 U.S.C. 154(b) by 953 days.

(21) Appl. No.: 13/572,094

(22) Filed: Aug. 10, 2012

(65) Prior Publication Data

US 2013/0041279 A1    Feb. 14, 2013

Related U.S. Application Data

(60) Provisional application No. 61/522,566, filed on Aug. 11, 2011.

(51) Int. Cl.
*A61B 5/08*      (2006.01)
*A61B 5/00*      (2006.01)
*A61B 5/1455*    (2006.01)

(52) U.S. Cl.
CPC ............ *A61B 5/082* (2013.01); *A61B 5/725* (2013.01); *A61B 5/14551* (2013.01)

(58) Field of Classification Search
None
See application file for complete search history.

(56) References Cited

U.S. PATENT DOCUMENTS

| | | | | |
|---|---|---|---|---|
| 6,428,483 | B1 * | 8/2002 | Carlebach | 600/532 |
| 6,589,188 | B1 * | 7/2003 | Street et al. | 600/538 |
| 6,942,622 | B1 * | 9/2005 | Turcott | A61B 5/0002 600/485 |
| 7,186,220 | B2 * | 3/2007 | Stahmann et al. | 600/529 |
| 2003/0045807 | A1 * | 3/2003 | Daniels et al. | 600/538 |
| 2004/0236240 | A1 * | 11/2004 | Kraus | A61B 5/0205 600/529 |
| 2006/0200035 | A1 * | 9/2006 | Ricci et al. | 600/513 |
| 2008/0072905 | A1 * | 3/2008 | Baker | A61B 5/0836 128/204.23 |
| 2008/0082018 | A1 * | 4/2008 | Sackner et al. | 600/538 |
| 2008/0269625 | A1 * | 10/2008 | Halperin et al. | 600/508 |
| 2008/0300500 | A1 * | 12/2008 | Reisfeld | A61B 5/0205 600/532 |
| 2011/0040713 | A1 * | 2/2011 | Colman | A61B 5/0836 706/16 |

* cited by examiner

*Primary Examiner* — Etsub D Berhanu
*Assistant Examiner* — Jairo H Portillo
(74) *Attorney, Agent, or Firm* — Nixon Peabody LLP (57) ABSTRACT

A method of diagnosis. The method can include the steps of sampling the breathing of a patient and from the sampling, obtaining a waveform corresponding to a pattern of the breathing of the patient in which the waveform is a repetitive waveform that is indicative of a carbon dioxide concentration in air expired by the patient. The method can also include the steps of processing the waveform to obtain a set of data that reflects the carbon dioxide concentration in the expired air and based on the processing of the waveform, detecting a potential adverse respiratory event in the patient.

12 Claims, 5 Drawing Sheets

SYSTEM AND METHOD FOR MONITORING PHYSIOLOGICAL FUNCTIONS

CROSS-REFERENCE TO RELATED APPLICATIONS

This application claims priority to U.S. Provisional Patent Application No. 61/522,566, filed Aug. 11, 2011 and entitled "SYSTEM AND METHOD FOR MONITORING PHYSIOLOGICAL FUNCTIONS", the contents of which are hereby incorporated by reference in their entirety.

FIELD OF THE INVENTION

The present invention relates to the field of monitoring physiological functions in general, and in particular to analysis and interpretation of the waveforms obtained in physiological measurements.

BACKGROUND OF THE INVENTION

Various processes exist to monitor physiological characteristics of a patient. For example, capnography is the monitoring of the concentration or partial pressure of carbon dioxide ($CO_2$) during a respiratory cycle. Its main development has been as a monitoring tool for use during anesthesia and intensive care. A graphical representation of a patient's ventilatory status for $CO_2$ concentration can be presented as a capnograph or capnogram, illustrating expiratory $CO_2$ concentration plotted against time or expired volume. The capnogram is a direct monitor of the inhaled and exhaled concentration or partial pressure of $CO_2$ and an indirect monitor of the $CO_2$ partial pressure in the arterial blood.

Chronic obstructive pulmonary disease (COPD) refers to chronic bronchitis and emphysema, two commonly co-existing diseases of the lungs in which the airways become narrowed. This condition leads to a limitation of the flow of air to and from the lungs causing shortness of breath. The limitation of airflow is normally irreversible and usually gets progressively worse over time.

Typically, a healthcare provider can look at the capnogram displayed on a monitor and interpret it by visual inspection. Visual evaluation and interpretation of the capnogram is typically done by qualitative pattern recognition. Pattern recognition is a technique in which a capnogram is visually compared to a set of abnormal capnograms, with a corresponding differential diagnosis for each abnormal shape. This process requires considerable skill and specialized knowledge on the part of the person doing the visual comparison and is useful only for conditions or diseases that result in a large-scale abnormality in capnogram shape that is clearly visible to the naked eye. Moreover, experts are predicting a shortage of qualified medical personnel in the future in view of continued population growth and greater access to healthcare.

SUMMARY OF THE INVENTION

A method and system of diagnosis is described herein. In one arrangement, the method can include the steps of sampling the breathing of a patient and from the sampling, obtaining a waveform corresponding to a pattern of the breathing of the patient in which the waveform is a repetitive waveform that is indicative of a carbon dioxide concentration in air expired by the patient. The method can also include steps of processing the waveform to obtain a set of data that reflects the carbon dioxide concentration in the expired air and based on the processing of the waveform, detecting a potential adverse respiratory event in the patient. In one embodiment, a period of the waveform can include a sawtooth wave component and a square wave component that corresponds to a capnographic pattern that is exhibited by patients with COPD.

As an example, processing the waveform can include the steps of identifying even harmonics present in the waveform and comparing the number of even harmonics present in the waveform with a predetermined threshold. If the number of even harmonics present in the waveform exceeds the predetermined threshold, the method can further include the step of generating an alert signal that indicates the presence of the potential adverse respiratory event. In this case, it may be necessary to only process the first half of a period of the waveform to identify the even harmonics that are present in the waveform.

As another example, processing the waveform may include the steps of identifying even and odd harmonics that are part of the waveform, comparing amplitudes of the even harmonics with amplitudes of the odd harmonics to obtain a first ratio and comparing the first ratio with a predetermined ratio. If the first ratio exceeds the predetermined ratio, the method can also include the step of generating a signal that indicates the presence of the potential adverse respiratory event. In this example, a full period of the waveform may be processed to identify the even and odd harmonics that are present in the waveform.

In another example, processing the waveform can include the steps of identifying even and odd harmonics in the waveform and determining whether the even harmonics are out of phase with the odd harmonics. If the even harmonics are out of phase with the odd harmonics, the method can further include the step of generating a signal that is indicative of the potential adverse respiratory event.

In yet another example, processing the waveform can include the steps of obtaining a cumulative probability distribution of the waveform and if the cumulative probability distribution of the waveform has a negative slope, generating an alert signal that indicates the presence of a potential adverse respiratory event. One or more periods of the waveform may be processed to obtain the cumulative probability distribution of the waveform.

As an option, the method can further include the steps of measuring an oxygen saturation level of the patient's blood and comparing the measured oxygen saturation level with a predetermined level to detect the potential adverse respiratory event. The method can further include the step of generating an alert that indicates the presence of the potential adverse respiratory event if both the processing of the waveform and the comparison of the oxygen saturation level indicate such a presence. Alternatively, processing the waveform consistent with the above discussion or analyzing oxygen saturation levels as described here may solely be used to detect the adverse respiratory event.

A system for diagnosing adverse respiratory events is also described herein. In one arrangement, the system can include a sensor that is configured to detect $CO_2$ in air that is exhaled by a patient and a processor that is coupled to the sensor. The sensor can include, for example, an infra-red light generator that causes light to pass through the air that is exhaled by the patient. The processor can receive signals from the sensor that are indicative of the $CO_2$ concentration in a breathing pattern of the patient. The processor can be operable to obtain a periodic waveform that corresponds to the breathing pattern, analyze the periodic waveform to produce data that is associated with the $CO_2$ concentration in the breathing pattern and compare the data with one or more known values to detect a potential adverse respiratory event in the patient. In particular, the periodic waveform may include both sawtooth wave components and square wave components, and the potential adverse respiratory event can be a breathing obstruction.

In one embodiment, the known value can be a predetermined number of even harmonics and as part of analysis of the periodic waveform, the processor can be further operable to detect even harmonics in the periodic waveform and compare the number of even harmonics with the known value. The processor can then notify an agent of the potential adverse respiratory event if the detected number of even harmonics is greater than the known value. In this example, the processor can perform the analysis on only the first half of a period of the periodic waveform.

In another example, the known value can be a predetermined ratio and, as part of the analysis of the periodic waveform, the processor can be further operable to determine amplitudes of both even and odd harmonics of the periodic waveform to form a measured ratio. The processor can then compare the measured ratio with the known value and can inform an agent of the potential adverse respiratory event if the measured ratio exceeds the known value. In this scenario, the processor can perform the analysis over the full period of the periodic waveform.

In another arrangement, the known value can be the presence of out of phase even harmonics and, as part of the analysis of the periodic waveform, the processor can be further operable to determine that even harmonics of the periodic waveform are out of phase with odd harmonics of the periodic waveform. In response to such detection, the processor can signal an agent of the potential adverse respiratory event.

In yet another example, the known value may be a negative slope and, as part of the analysis, the processor can be further operable to generate a cumulative probability distribution of the periodic waveform, determine a slope of the cumulative probability distribution of the periodic waveform and compare the slope to the known value. If the slope exceeds the known value, the processor can further signal an agent of the potential adverse respiratory event.

The system may also include a pulse oximeter that is coupled to the processor and that is configured to measure a level of oxygen saturation in the patient's blood. If such an option is accepted, the processor can be further operable to compare the measured level of oxygen saturation with a predetermined level to detect a potential adverse respiratory event and to generate an alarm that indicates the presence of the potential adverse respiratory event if the comparison of the data with the known value also indicates the potential adverse respiratory event. Of course, analyzing the waveform consistent with the above discussion or analyzing oxygen saturation levels as described here may solely be used to detect the adverse respiratory event.

A method of classifying a capnograph signature is also described herein. This method can include the steps of monitoring a breathing pattern of a patient, converting the breathing pattern into a periodic digital waveform and analyzing the periodic waveform to detect the presence of a sawtooth wave component in the periodic digital waveform. Such a presence may indicate a potential adverse respiratory event. Analyzing the periodic digital waveform may include detecting an adverse number of even harmonics in the waveform, detecting an adverse ratio of even and odd harmonics in the waveform, detecting even harmonics in the waveform that are out of phase with odd harmonics that are in the waveform or detecting a negative slope associated with a cumulative probability distribution of the waveform. The method can also include the step of generating an alarm signal based on the analysis of the periodic digital waveform. In one particular example, the alarm signal may be generated only if a level of oxygen saturation for the patient also falls below a predetermined threshold.

A method of monitoring physiological functions in a patient is also described herein. This method can include the steps of receiving input signals associated with one or more physiological functions of a patient, converting the input signals into a digital periodic waveform and treating the digital periodic waveform as one or more non-sinusoidal waveforms. As such, the digital periodic waveform can be analyzed in a fashion that is available for the non-sinusoidal waveform. As an example, the non-sinusoidal waveform may include both sawtooth wave components and square wave components. The method can also include the step of selectively generating an alert that a potential adverse health event exists in the patient based on the analysis of the digital periodic waveform.

As an example, the physiological function can be a breathing process of the patient and the adverse health event is an obstructed airway of the patient. In addition, analyzing the digital periodic waveform can include detecting an adverse number of even harmonics in the waveform, detecting an adverse ratio of even and odd harmonics in the waveform, detecting even harmonics in the waveform that are out of phase with odd harmonics that are in the waveform or detecting a negative slope associated with a cumulative probability distribution of the waveform.

A physiological monitoring unit is also described herein. The monitoring unit may include a receiver that is configured to receive input signals that correspond to one or more physiological functions of a patient and may also include a converter coupled to the receiver in which the converter is configured to convert the input signals into a digital periodic waveform. The monitoring unit may also have a processor coupled to the converter in which the processor can be operable to analogize the digital periodic waveform to one or more non-sinusoidal waveforms and perform an analysis on the digital periodic waveform in accordance with a process that is applicable to the non-sinusoidal waveforms. The processor may also selectively generate an alert that a potential adverse health event exists in the patient based on the analysis of the digital periodic waveform. In one example, the non-sinusoidal waveform may include both sawtooth wave components and square wave components.

Additional aspects will be set forth in the description which follows, and in part will be obvious from the description, or may be learned by practice of the embodiment. The aspects will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

Several embodiments are shown in the drawings. It is expressly noted, however, that the subject matter herein is not necessarily limited to the arrangements and instrumentalities shown in the drawings.

DETAILED DESCRIPTION

As noted earlier, reviewing capnographic patterns of patients requires significant skill on the part of medical personnel, and the potential for a shortage of such persons in the future is likely. In addition, these patterns can only be reviewed intermittently, and obstructed breathing or the onset of such a condition may not be detected for an extended—and undesirable—period of time. To overcome these issues, a method and system of diagnosis are described herein. As an example, the method can include the steps of sampling the breathing of a patient and from the sampling, obtaining a waveform corresponding to a pattern of the breathing of the patient in which the waveform is a repetitive waveform that is indicative of a $CO_2$ concentration in air expired by the patient. The method can also include the steps of processing the waveform to obtain a set of data that reflects the $CO_2$ concentration in the expired air and based on the processing of the waveform, detecting a potential adverse respiratory event in the patient.

This process provides an economical and easily available means of detecting respiratory problems like COPD or other potential adverse physiological events. In addition, the screening could indicate susceptibility or an early stage of COPD well before traditional symptoms are evident. Implementation of this method would also permit individuals who need frequent monitoring of the severity of a diagnosed COPD condition to be provided with the proper and continuous medical oversight that would be required.

The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled" as used herein is defined as connected, although not necessarily directly, and not necessarily mechanically. That is, "coupled" may also include two or more components that are wirelessly connected together.

The term "patient" can be defined as any living thing that requires or may require medical attention and includes humans and non-human animals. The terms "breathing pattern" or "pattern of breathing" mean the current and substantially consistent form of breathing exhibited by a patient over a period of time. A "waveform" is defined as the shape of a graph of one or more varying quantities against time or distance. A "periodical" or "repetitive" waveform means any graph that substantially repeats itself after a substantially fixed interval of time. The term "potential adverse respiratory event" is defined as any possible obstruction or interference in a patient's normal breathing pattern, and the term "potential adverse health event" means any possible medical condition that may threaten the well-being of a patient. A "sensor" is defined as any device capable of receiving or detecting stimuli and in response to such receipt or detection, transmitting signals in response to a measuring or control instrument. A "processor" is defined as any electronic device capable of receiving data and performing prescribed operations on the data, including operations that are described herein. An "agent" is defined as any human entity or machine capable of receiving or detecting a signal that may indicate the presence of an adverse medical condition of a patient. The term "breathing obstruction" is defined as any condition in which a patient's normal breathing pattern is hampered or impeded.

The term "physiological function" is defined as any activity or process of a living being and its parts, including physical and chemical processes of the living being. The term "non-sinusoidal waveform" means a waveform that is not a pure sine wave. One example of a non-sinusoidal waveform is one that contains multiple sine waves of varying frequencies.

Figure 1:
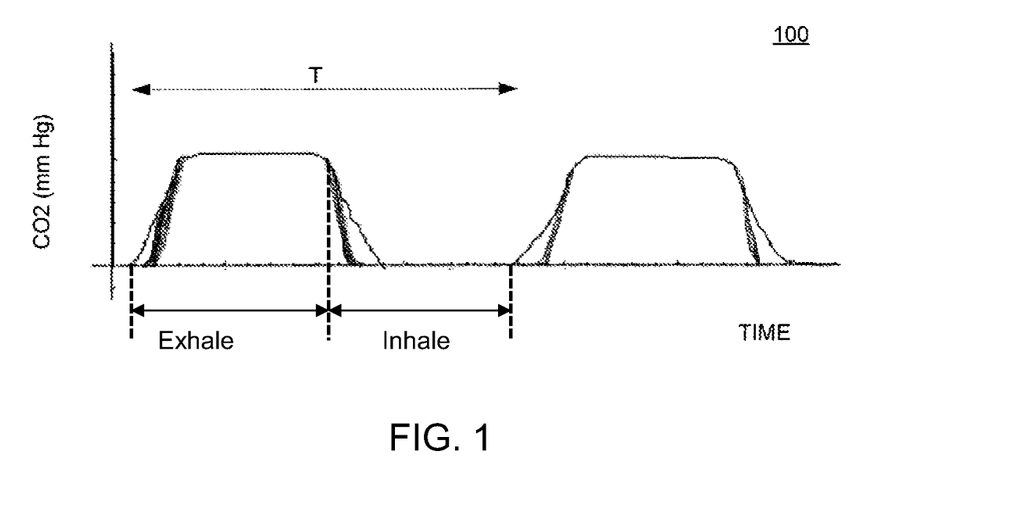
FIG. 1 is an illustration of a capnogram representing a healthy patient's $CO_2$ concentration plotted against time.

Referring to FIG. 1, a graph 100 is shown that reflects a breathing pattern of a healthy individual in which $CO_2$ concentration is plotted against time. Here, the flat portion of the graph represents inhalation by the patient, while the raised section represents the expiration of air by the patient. As can be seen, the graph 100 is repetitive in nature and symmetric (i.e., the rise time and the fall time of the waveform are substantially similar) and has a period T and a frequency f. In addition, this individual appears to be expel $CO_2$ at a near constant rate for roughly fifty percent of the overall breathing cycle.

Figure 2:
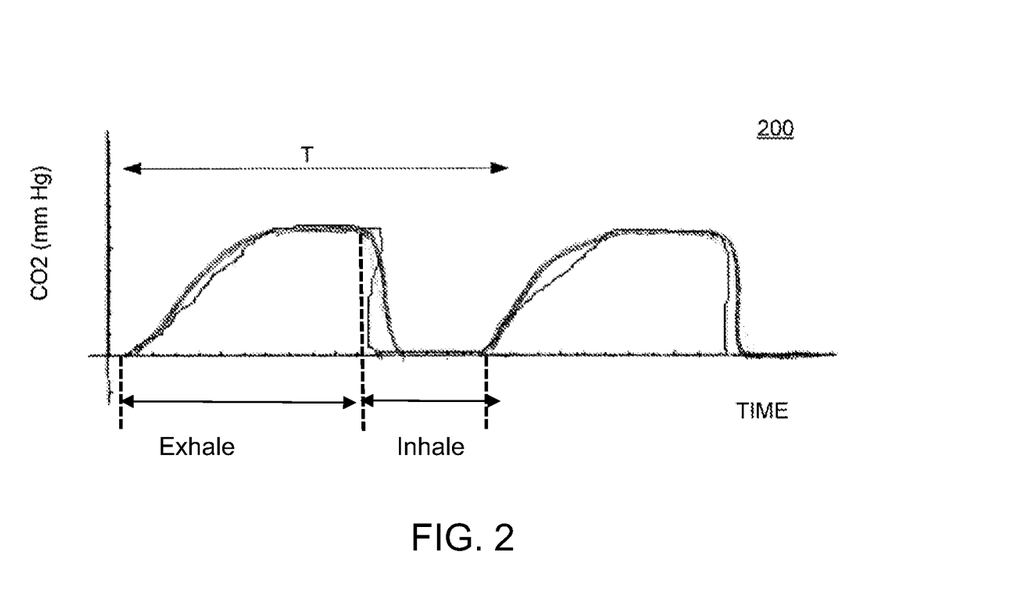
FIG. 2 is an illustration of a capnogram representing $CO_2$ concentration plotted against time for a patient suffering from a breathing obstruction.

Referring to FIG. 2, a graph 200 is shown that displays the breathing pattern of a person afflicted with a breathing obstruction. Similar to the graph 100 of FIG. 1, the breathing cycle here is repetitive and has a period T and a frequency f. However, the waveform is not symmetric (i.e., the rise time and the fall time of the waveform are not substantially similar). In other words, the $CO_2$ expulsion rate for this person is reduced near the beginning of the exhalation portion by the obstruction (long rise time) and eventually increases as the person's airway is cleared or expands. Moreover, the time of the exhalation portion is greater in comparison to the time of the inhalation portion, which is a result of the necessity to fully purge the lungs of $CO_2$. Unfortunately, this person may be suffering from COPD and may require careful monitoring to ensure proper medical attention is given.

Figure 3:
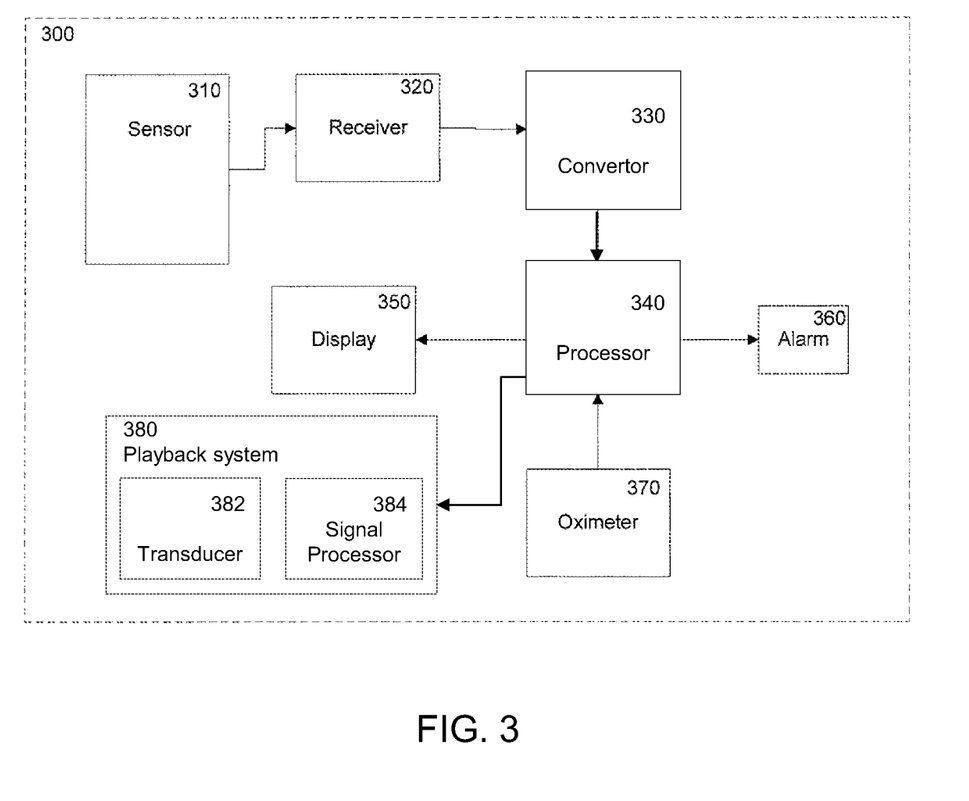
FIG. 3 is a system that is useful for diagnosing adverse respiratory or other health-related events.

Referring to FIG. 3, a system 300 for monitoring various physiological functions such as breathing is shown. The system 300 may include a sensor 310, which can be used to detect various stimuli, such as $CO_2$ in air that is exhaled by a patient. In one particular example but without limitation, the sensor may be a nondispersive infrared (NDIR) sensor. Such a sensor can include, for example, an infrared source, a light tube, an interference (wavelength) filter (optional), and an infrared detector, and supporting electronics. In operation, the exhaled air is directed through or diffuses into the light tube and which infrared light from the infrared source is directed therein. Afterwards, the infrared detector generates a signal indicative of the amount of light received and, based on this signal, the electronics can generate a measurement of the absorption of the characteristic wavelength of light. In another particular example but without limitation, the sensor may be a chemical sensor with $CO_2$ sensitive layers. However, the various embodiments are not limited to these particular configurations and any other type of sensor can be used in the various embodiments without limitation.

The sensor 310 may be positioned in any suitable location or other piece of equipment to enable the sensor 310 to perform its function. The sensor 310 can be coupled to a receiver 320, which can serve as an interface between the sensor 310 and the rest of the components of the system 300, if so desired. The coupling between the sensor 310 and the receiver 320 may be a hard-wired connection, a wireless connection, or any combination thereof. A converter 330 may also be coupled to the receiver 320, and the converter 330 can convert the signals received by the receiver 320 into digital form. As an example, the sensor 310 may generate a waveform that is indicative of a breathing pattern of a patient, similar to those shown in FIG. 1 or 2, and the converter 330 can convert this waveform into a periodic digital waveform.

The converter 330 can input to a processor 340 the digital waveforms that it produces, and, as will be explained later, the processor 340 can analyze these waveforms to detect possible adverse health events. As an added convenience, the processor 340 may prepare and transmit the digital waveforms for display on a display unit 350. If the processor 340 determines that a potential adverse health event exists, the processor 340 can generate an alarm or alert signal and can forward this signal to an alarm unit 360.

Optionally, a pulse oximeter 370 can be included as part of the system 300. As is known in the art, a pulse oximeter may measure the level of oxygen saturation in the blood of a patient. If this level is too low, the patient may be suffering from a breathing obstruction. The pulse oximeter can forward the measured level to the processor 340, which can compare the measured level of oxygen saturation with a predetermined level to detect a potential adverse respiratory event. In this configuration, the measurements provided by the pulse oximeter 370 can be used as a complement to the monitoring of the $CO_2$ concentration from the patient or, alternatively, can be used solely as a way to detect the potential adverse events. Although not shown here, the pulse oximeter 370 may also be coupled to the processor 340 through the receiver 320 and the converter 330 or through any other suitable means.

It must be noted that all or a portion of the components shown in the system 300 may be implemented as a single integrated unit. For example, the system 300 may be a portable device that can be attached to, for example, a breathing-assistance device, such as an endrotracheal tube or a breathing mask. However, the components shown in system 300 may also implemented using two or more separate components. For example, the sensor 310 and the pulse oximeter 370 may be discrete components that are distinct and separate from the remaining components.

Figure 4:
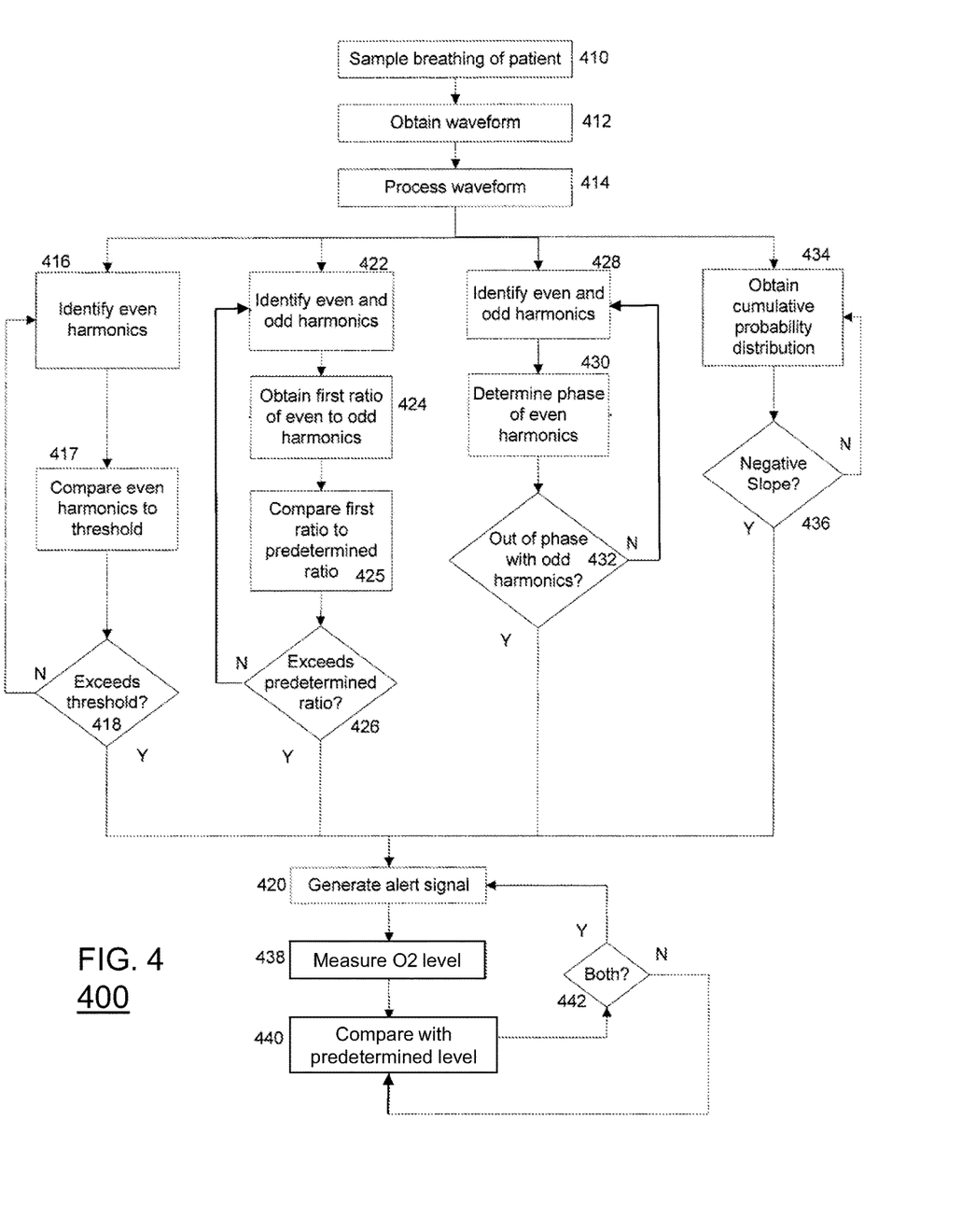
FIG. 4 is flowchart for a method for a diagnosis.

Referring to FIG. 4, a method 400 of diagnosis is illustrated. When describing this method, reference may be made to FIG. 3, although it is understood that the method 400 may be practiced in other suitable systems. It must be noted that the described method 400 is not necessarily limited to these particular steps, as the method 400 may contain a greater or fewer number of steps in comparison to what is pictured. Moreover, the method 400 is not limited to the particular order illustrated here.

Method 400 begins at step 410. At step 410, the breathing of a patient may be sampled, and at step 412, a waveform may be obtained from the sampling in which the waveform corresponds to a pattern of the breathing of the patient. In one arrangement, the waveform may be the repetitive or periodic waveform that is indicative of $CO_2$ concentration in air that is exhaled by the patient and as detected by the sensor 310. Each of the graphs 100, 200 of FIGS. 1 and 2 may be considered examples of this process, although it is understood that these waveforms are not the only ones that may apply here. Further, $CO_2$ concentration is not the only process that may be monitored for purposes of monitoring patient breathing. Rather, any other measurement associated with patient breathing can be utilized in the various embodiments. However, for ease of illustration, the remainder of the method will be described with respect to measurements of $CO_2$ concentration.

At step 414, the waveform may be processed to obtain a set of data that reflects the $CO_2$ concentration in the exhaled air. Based on the processing of the waveform, a potential adverse respiratory event in the patient may be detected. There are several ways for the waveform to be processed to obtain the set of data that may indicate breathing trouble. For example, referring to step 416, even harmonics that are present in the waveform can be identified. Thereafter, the number of even harmonics can be compared with a predetermined threshold, as shown at step 417. At decision block 418, it can be determined whether the number of even harmonics exceeds the predetermined threshold. If this threshold is not exceeded, the method 400 can return to step 416 to resume monitoring and processing of the even harmonics. If the threshold is exceeded, an alert signal can be generated that indicates the presence of a potential adverse respiratory event, as shown at step 420. This can be illustrated with respect to FIGS. 1 and 2.

Figure 5:
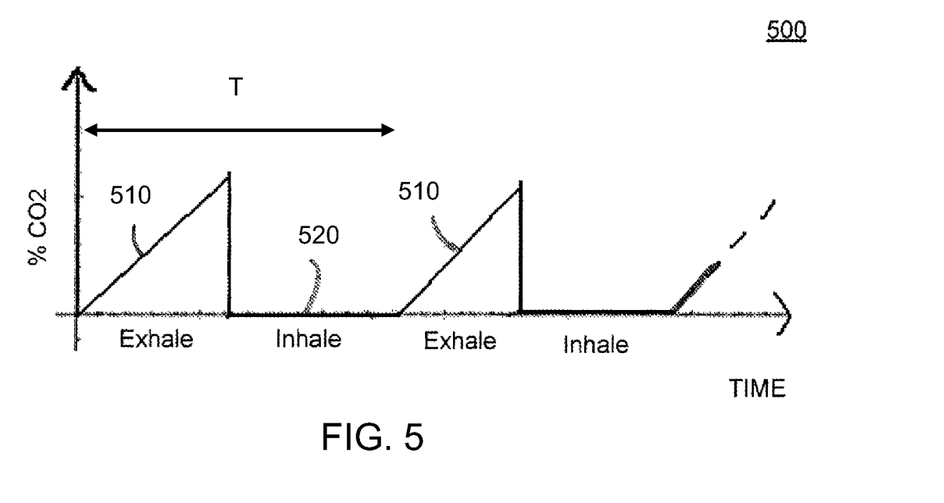
FIG. 5 is a graph of a waveform having non-sinusoidal components.

First, focusing on the graph 100 of FIG. 1, it can be seen that the breathing pattern of a healthy patient closely mimics a square or rectangular waveform, which contains only odd integer harmonics. In contrast, the graph 200 partially resembles a sawtooth waveform, which contains even harmonics. In fact, the graph 200 may include a sawtooth wave component and a square wave component, an example of which is shown in FIG. 5. Here, a waveform 500 ($CO_2$ concentration against time) has a period T in which the first component, related to an exhalation process, is a sawtooth wave component 510 and the second component, related to an inhalation process, is a square wave component 520. As an example, this waveform 500 can correspond to a capnographic pattern that may be exhibited by patients with COPD.

In view of this configuration, the waveform generated by the patient can be treated as one or more non-sinusoidal waveforms, which can allow for several analyses to be performed. For example, when monitoring a patient, the processor 340 can analyze the first half of a period for the waveform from the patient for even harmonics and can compare the detected number of even harmonics with a known value. If the number of detected even harmonics exceeds the known value, the breathing waveform may be reflective of the patient suffering from a breathing obstruction. This known value can be as low as zero such that the detection of any even harmonics would exceed the relevant threshold. In such a case, the processor 340 can generate an alert signal, which can trigger any number of suitable mechanisms to bring attention to the potential breathing problem. For example, the alert signal could be displayed on the display 350, along with an audible alarm if desired, or simply transmitted to the alarm unit 360. The alert signal could also be used to trigger an action in a machine in response to the detected potential event, such as a unit that dispenses drugs or takes some corrective action to assist in the stabilization of the patient.

Referring back to the method 400, two more examples of how the waveform can be processed will be presented. At step 422, even and odd harmonics that are part of the waveform can be identified, and the amplitudes of these harmonics can be compared to obtain a first ratio, as shown at step 424. At step 425, the first ratio can be compared with a predetermined ratio. At decision block 426, if the first ratio does not exceed the predetermined ratio, then the method can resume monitoring of odd and even harmonics at step 422. If the first ratio does exceed the predetermined ratio, however, a signal can be generated that indicates that a potential adverse respiratory event exists, as shown at step 420. The predetermined ratio can be predefined in some case, either generally for a group or from baseline measurements of the patient. In other cases, the predetermined ratio can be based on previous measurements. That is, the ratio can be computed based on initial measurements to establish the baseline measurement. Thereafter, if the breathing of the patient degrades, the ratio can be utilized to generate an alert signal. As described above, the alert signal can be used to trigger an action in a machine in response to the detected potential event, such as a unit that dispenses drugs or takes some corrective action to assist in the stabilization of the patient.

In another example, the phase of the harmonics can be evaluated. For example, at step 428, even and odd harmonics in the waveform can be identified. Thereafter, at step 430, it can be determined whether the even harmonics are out of phase with the odd harmonics. If the harmonics are in phase at decision block 432, the method 400 can return to step 428 to continue monitoring. If the harmonics are out of phase at decision block 432, then the method 400 can proceed to step 420, where again an alert signal can be generated.

For example, referring back to FIG. 5, in these cases, the full period T of the waveform can analyzed. Because the waveform contains both sawtooth and square wave components, both even and odd harmonics may be present. The processor 340 (see FIG. 3) may determine the amplitudes of these harmonics to obtain a first ratio and then compare this ratio to a known ratio value. In one arrangement, a higher ratio would indicate the presence of strong even harmonics, which is reflective of a breathing pattern hindered by an obstruction, as explained above. If the first ratio exceeds the predetermined ratio, the processor 340 may take corrective action, similar to that described previously. It is understood that the first ratio can be the ratio of even to odd harmonics or odd to even harmonics. In the case of the latter, exceeding the predetermined ratio can mean having a ratio that is lower than the predetermined ratio.

Additionally, the processor 340 may detect that the even harmonics are out of phase with the odd harmonics. In one particular example, being out of phase can mean that the even harmonics are 180 degrees out of phase with the odd harmonics, although it is understood that other values may be applicable here. In that case, being out of phase may refer to being out of phase greater than a predetermined value. If the processor detects the out of phase condition, it may also perform actions similar to those already described above.

Referring back to the method 400, yet another example of how the waveform may be processed to detect a potential adverse respiratory event will be shown. At step 434, a cumulative probability distribution of the waveform can be obtained. Thereafter, at decision block 436 the slope of the distribution can be evaluated. If the distribution has a non-negative slope at decision block 436, then the method can resume monitoring at step 434. If the distribution has a negative slope at decision block 436, an alert signal can again be generated at step 420 in which the signal indicates a potential adverse event exists.

Figure 6:
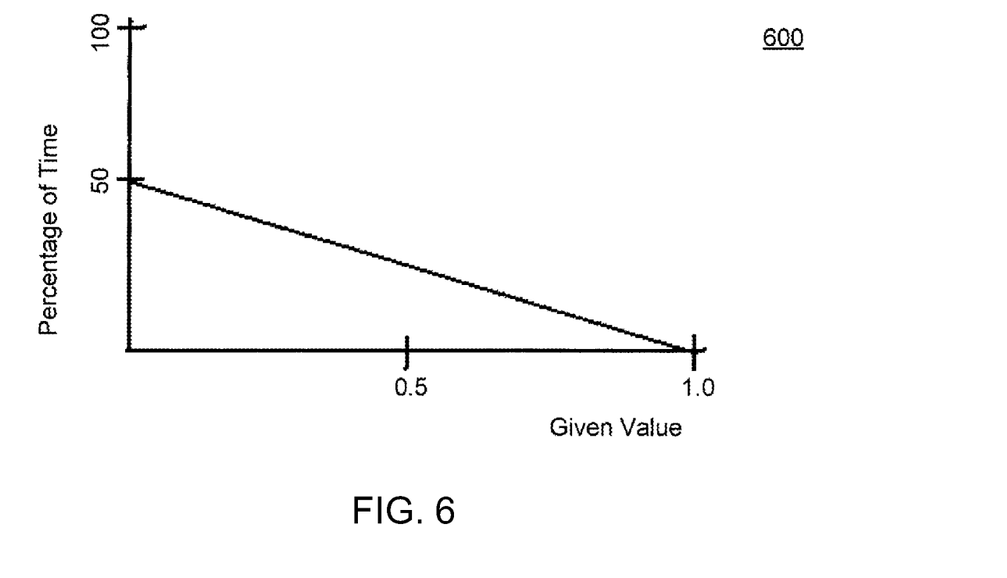
FIG. 6 is a graph of a cumulative probability distribution for a waveform.

As is known in the art, a cumulative probability distribution of a waveform is a plot of the probability that the waveform will be above a given fraction of the peak amplitude of the waveform. As an example, a square wave with a duty cycle of fifty percent will exceed a given level of the waveform a consistent fifty percent of the time. Thus, the pattern of breathing exhibited by a healthy patient may have a substantially flat distribution graph. The breathing pattern exhibited by a patient suffering from a breathing obstruction, such as COPD, however, may display a graph with a negative slope. For purposes herein, a negative slope should not include a flat (or zero slope) graph. Referring to FIG. 6, an example of a cumulative probability distribution 600 is shown. The values on the Y-axis represent the percentage of time that a waveform is above a given fraction of its peak amplitude, while the values on the X-axis refer to the fractional values of the peak amplitude of the waveform.

The distribution 600 shown in FIG. 6 is the distribution of the waveform 500 shown in FIG. 5, which, as has been already explained, can indicate a breathing problem in a patient. As can be seen, for the lower fractional values of the peak amplitude, the amount of time that the waveform 500 will be above such lower fractional values is higher when compared to higher fractional values. Thus, this distribution 600 has a negative slope, which may be a sign of a potential adverse respiratory event. The processor 340 can detect this negative slope and can take one or more steps to help alleviate the event. In one arrangement, the value for the negative slope of the distribution 600 can be compared to a known value, and it can be determined that an adverse event exists only if the negative slope is lower than the known value. Any suitable number of periods or cycles of the waveform can be analyzed for this particular process.

In one arrangement, any of the four previously described processes can be performed solely to detect the potential adverse event. As an alternative, any suitable combination of two or more of the four processes can be performed to ensure that such a condition does exist. Other methods of measuring physiological functions may be used to bolster the accuracy of the determination of an adverse health-related event. For example, a pulse oximeter may be used in combination with any of the processes described above, if so desired.

Referring back to the method 400, once an alert signal is generated at step 420, the method can proceed to step 438. At step 438, the level of oxygen saturation in the blood of the patient can be measured, and this level can be compared with a predetermined level to detect a potential adverse respiratory event, as shown at step 440. This predetermined level can be a predefined value for a group or a baseline value for the patient. Alternatively the predetermined level can be computed value based on initial measurements. At decision block 442, if both the processing of the waveform and the comparison of the oxygen saturation level indicate the presence of the adverse event, then an alert can be generated, as shown at step 420. If both tests do not produce a result that shows a potential adverse event, then the alert may not be generated, and the method 400 can resume at step 440.

It must be noted that in some cases a different alert signal can be generated when both the processing of the waveform and the comparison of the oxygen saturation level indicate the presence of the adverse event. Thus, several types of alert signals may be generated.

For example, if desired, the pulse oximeter 370 can monitor the patient's level of oxygen saturation, and the oximeter 370 (or the processor 340) can compare the measured level with a predetermined value of oxygen saturation. If the measured level is below the known value, then the oximeter 370 can signal the processor 340 that a potential adverse respiratory event is present. In response, the processor 340 can determine whether the processing of the waveform 500 has also indicated a potential adverse event. If so, the processor 340 may take appropriate steps to address the patient's condition. Of course, it is not necessary for both the processing of the waveform and the oxygen saturation readings to indicate a potential adverse event, as either one by itself may lead to such a conclusion.

As explained above, a patient's breathing and/or oxygen saturation levels may be monitored—such as by analyzing the periodic waveforms generated by these processes—to detect potential adverse respiratory events. It must be noted, however, that the subject matter described herein is not so limited. In particular, any physiological function of a patient that generates a substantially periodic waveform that contains one or more components that are substantially consistent with one or more non-sinusoidal waveforms can be monitored in a similar fashion. That is, any suitable portion of a periodic waveform generated from a physiological function of a patient can be treated like a relevant non-sinusoidal waveform, which presents an opportunity to perform an analysis on the patient's periodic waveform in a fashion that is available for the applicable non-sinusoidal waveform. This method can assist in monitoring for a wide variety of adverse health-related events.

Separately or in addition to the methods described above, the capnographic waveforms described herein can be used to audibly monitor a status of the patient. For example, the system of FIG. 3 can include a playback system 380 configured to audibly play back the stored, comparatively slow, capnographic waveforms at a higher speed, possibly normalized to a given preset period, such that it could be analyzed and diagnosed by a trained listener. Sawtooth-like waveforms and square or rectangular waveforms, when reproduced at audible frequencies, have distinctive sounds as unique as the tones of particular musical instruments. Further, the human ear is also capable of discerning waveforms where odd harmonics or even harmonics predominate as distinct from one another. In some cases, playback can be enhanced for the ear by audio filtering or enhanced for specific diagnostics by frequency selecting a specific spectral range. Thus, the playback system 380 can not only include a transducer 382 for reproducing the sounds, but also a signal processor 384 for generating and conditioning the audio signal for the transducer 382. In particular, the signal process can provide frequency dependent filtering can emphasize specific portions of the sound spectrum for easier human recognition. In some cases, the signal processor 384 can be incorporated into processor 340. Further, the playback system can be configured to allow the speed of playback can be varied by the diagnostician.

Thus, alternatively or in combination with monitoring of capnographic waveforms described in FIG. 4, capnographic waveforms can be audibly monitored to monitor the status of a patient. In some embodiments, the audible monitoring can be utilized at all times, such as in a hospital or other medical environment. Thus, if the care provider begins to hear sounds associated with changes in breathing in a patient, the care provider can take appropriate action.

In a particular embodiment, the analysis system can be used by a care provider or a patient to determine whether an administered treatment, including drug treatments and other treatments, has been performed correctly. In such cases, the care provider or patient can be trained to recognize the distinctive sounds of correct or incorrect treatment. Thus, if listener fails to hear the correct sounds after a treatment is administered, appropriate corrective measures can be taken. For example, additional treatment can be provided or medical personnel can be alerted by the listener.

In some embodiments, an analysis system, audible or otherwise, can be associated with a drug dispensing unit. A drug dispensing unit can be a unit that provides access to one or more among solid drug treatments (e.g., pills and capsules), liquid drug treatments (e.g., oral liquid or injectable drugs), or gas-based (e.g., inhaler-delivered drugs). Such an analysis system can be configured to provide a warning or a confirmation, based on the capnographic waveforms, to give feedback as to proper administration and dosage. For example, the analysis system can provide audio indicators, visual indicators, tactile indicators, or any combination thereof, to designate when sufficient treatment has occurred or if under- or over-treatment has occurred. In some cases, if improper dosage has occurred, the dispenser can be configured to prevent further administration of one or more types of drugs to prevent the accumulation of effects of improper dosage.

In some cases, the dispenser unit can be further configured to store the capnographic waveforms of multiple administrations. Thus, this can allow monitoring of treatment over time. For example, if the effect of a treatment is a change in the capnographic waveform, the change in the audio signal can be utilized to determine that a treatment has occurred. The time and date of such a treatment can then be recorded. Further, the effects of dosage, weighted by time and capnographic waveform response, can also be recorded. Thereafter, such data could be analyzed by a care provider to determine responsiveness of a patient to a treatment and to determine whether the patient is receiving a proper dosage.

Figure 7:
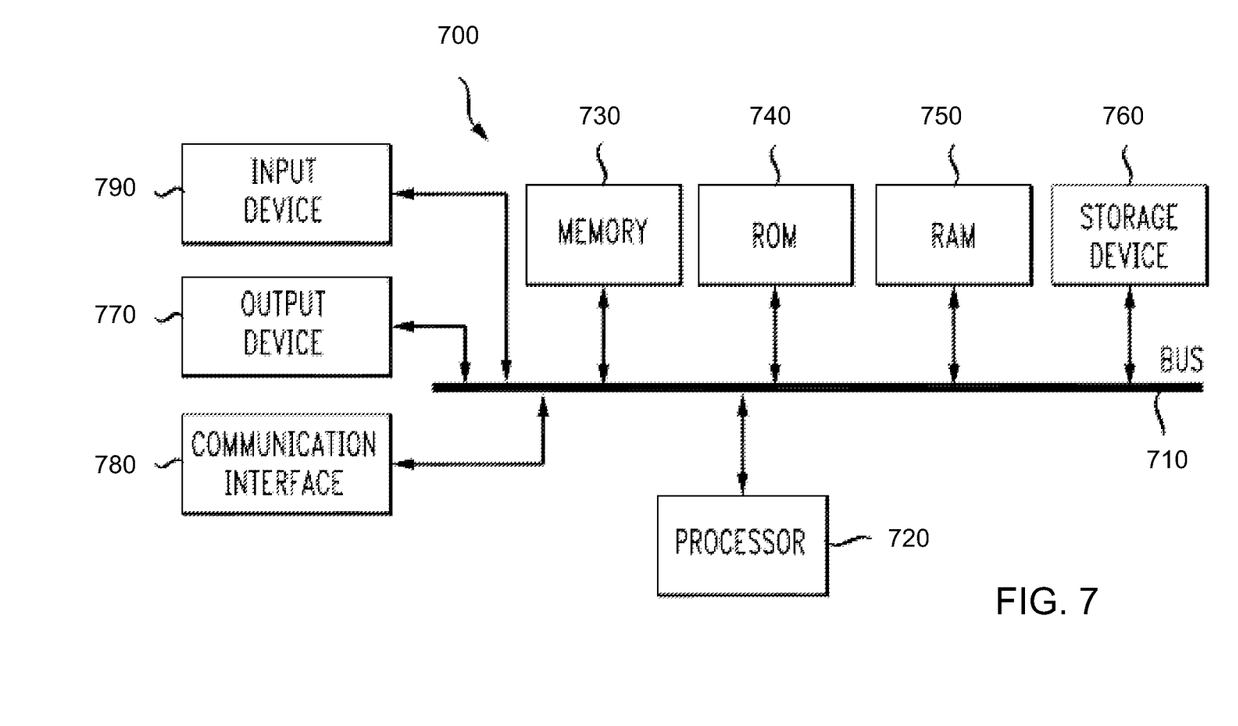
FIG. 7 is a diagram of the general components of a computer system adapted to perform the method of the present invention.

With reference to FIG. 7, a general-purpose computing device 700 which can be portable or stationary is shown, including a processing unit (CPU) 720 and a system bus 710 that couples various system components including the system memory such as read only memory (ROM) 740 and random access memory (RAM) 750 to the processing unit 720. Other system memory 730 may be available for use as well. It can be appreciated that the system may operate on a computing device with more than one CPU 720 or on a group or cluster of computing devices networked together to provide greater processing capability. The system bus 710 may be any of several types of bus structures including a memory bus or memory controller, a peripheral bus, and a local bus using any of a variety of bus architectures. A basic input/output (BIOS) stored in ROM 740 or the like, may provide the basic routine that helps to transfer information between elements within the computing device 700, such as during start-up. The computing device 700 further includes storage devices such as a hard disk drive 760, a magnetic disk drive, an optical disk drive, tape drive or the like. The storage device 760 is connected to the system bus 710 by a drive interface. The drives and the associated computer readable media provide nonvolatile storage of computer readable instructions, data structures, program modules and other data for the computing device 700. In one aspect, a hardware module that performs a particular function includes the software component stored in a tangible computer-readable medium in connection with the necessary hardware components, such as the CPU, bus, display, and so forth, to carry out the function. The basic components are known to those of skill in the art and appropriate variations are contemplated depending on the type of device, such as whether the device is a small, handheld computing device, a desktop computer, or a large computer server.

Although the exemplary environment described herein employs a hard disk, it should be appreciated by those skilled in the art that other types of computer readable media which can store data that is accessible by a computer, such as magnetic cassettes, flash memory cards, digital versatile disks, cartridges, random access memories (RAMs), read only memory (ROM), a cable or wireless signal containing a bit stream and the like, may also be used in the exemplary operating environment.

To enable user interaction with the computing device 700, an input device 790 represents any number of input mechanisms, such as a microphone for speech, a touch-sensitive screen for gesture or graphical input, keyboard, mouse, motion input, speech and so forth. The device output 770 can also be one or more of a number of output mechanisms known to those of skill in the art. For example, video output or audio output devices which can be connected to or can include displays or speakers are common. Additionally, the video output and audio output devices can also include specialized processors for enhanced performance of these specialized functions. In some instances, multimodal systems enable a user to provide multiple types of input to communicate with the computing device 700. The communications interface 780 generally governs and manages the user input and system output. There is no restriction on the disclosed methods and devices operating on any particular hardware arrangement and therefore the basic features may easily be substituted for improved hardware or firmware arrangements as they are developed. For clarity of explanation, the illustrative system embodiment is presented as including individual functional blocks (including functional blocks labeled as a "processor"). The functions these blocks represent may be provided through the use of either shared or dedicated hardware, including, but not limited to, hardware capable of executing software. For example the functions of one or more processors presented in FIG. 7 may be provided by a single shared processor or multiple processors. (Use of the term "processor" should not be construed to refer exclusively to hardware capable of executing software.) Illustrative embodiments may include microprocessor and/or digital signal processor (DSP) hardware, read-only memory (ROM) for storing software performing the operations discussed below, and random access memory (RAM) for storing results. Very large scale integration (VLSI), field-programmable gate array (FPGA), and application specific integrated circuit (ASIC) hardware embodiments may also be provided.

The logical operations of the various embodiments are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits.

Other implementations according to these examples include computer-readable media for carrying or having computer-executable instructions or data structures stored thereon. Such computer-readable media can be any available media that can be accessed by a general purpose or special purpose computer. By way of example, and not limitation, such tangible computer-readable media can include RAM, ROM, EEPROM, CD-ROM or other optical disk storage, magnetic disk storage or other magnetic storage devices, or any other medium which can be used to carry or store desired program code means in the form of computer-executable instructions or data structures.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures that perform particular tasks or implement particular abstract data types. Computer-executable instructions, associated data structures, and program modules represent examples of the program code means for executing steps of the methods disclosed herein. The particular sequence of such executable instructions or associated data structures represent examples of corresponding acts for implementing the functions described in such steps.

Those of skill in the art will appreciate that other embodiments of the invention may be practiced in network computing environments with many types of computer system configurations, including personal computers, hand-held devices, multi-processor systems, microprocessor-based or programmable consumer electronics, network PCs, mini-computers, mainframe computers, and the like. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Communication at various stages of the described system can be performed through a local area network, a token ring network, the Internet, a corporate intranet, 802.11 series wireless signals, fiber-optic network, radio or microwave transmission, etc. Although the underlying communication technology may change, the fundamental principles described herein are still applicable.

The various embodiments described above are provided by way of illustration only and should not be construed as limiting. Those skilled in the art may recognize various modifications and changes that may be made while following the example embodiments and applications illustrated and described herein, and without departing from the true spirit and scope of the present disclosure.

What is claimed is:

1. A system for analyzing a breath sample comprising:
a carbon dioxide sensor configured to receive the breath sample and generate a sensor output indicating a carbon dioxide measurement in the breath sample;
a signal converter communicatively coupled to the carbon dioxide sensor via a data receiver, wherein the signal converter is configured to process the sensor output and output a digital signal;
a processor device communicatively coupled to the signal converter and a transducer, wherein the processor device is configured to:
  receive the digital signal;
  generate a periodic waveform based on the received digital signal, wherein the periodic waveform indicates a carbon dioxide concentration in the breath sample;
  analyze the periodic waveform to generate a dataset of the carbon dioxide concentration in the breath sample, wherein the dataset includes even harmonics;

detect an adverse respiratory event in the dataset by:
  determining that a number of the even harmonics in the dataset exceeds a pre-defined threshold;
  identifying the adverse respiratory event upon determining that the number of the even harmonics in the dataset exceeds the pre-defined threshold; and
  generating a control signal directing the transducer to produce an audible alert signal that indicates the presence of the adverse respiratory event.

2. The system according to claim 1, further comprising a pulse oximeter communicatively coupled to the processor device, wherein the pulse oximeter is configured to measure a level of oxygen saturation.

3. The system according to claim 1, wherein the carbon dioxide sensor comprises an infra-red light emitter that passes light through the breath sample.

4. A system for analyzing a breath sample comprising:
a carbon dioxide sensor configured to receive the breath sample and generate a sensor output indicating a carbon dioxide measurement in the breath sample;
a signal converter communicatively coupled to the carbon dioxide sensor via a data receiver, wherein the signal converter is configured to process the sensor output and output a digital signal;
a processor device communicatively coupled to the signal converter and a transducer, wherein the processor device is configured to:
  receive the digital signal;
  generate a periodic waveform based on the received digital signal, wherein the periodic waveform indicates a carbon dioxide concentration in the breath sample;
  analyze the periodic waveform to generate a dataset of the carbon dioxide concentration in the breath sample, wherein the dataset includes even harmonics and odd harmonics;
  detect an adverse respiratory event in the dataset by:
    determining amplitudes of the even harmonics in the dataset;
    determining amplitudes of the odd harmonics in the dataset;
    determining a first ratio based on the amplitudes of the even harmonics and the amplitudes of the odd harmonics;
    determining that the first ratio exceeds a predetermined ratio;
    identifying the adverse respiratory event based on the determining that the first ratio exceeds the predetermined ratio; and
    generating a control signal directing the transducer to produce an audible alert signal that indicates the presence of the adverse respiratory event.

5. The system of claim 4, further comprising a pulse oximeter communicatively coupled to the processor device, wherein the pulse oximeter is configured to measure a level of oxygen saturation.

6. The system according to claim 4, wherein the carbon dioxide sensor comprises an infra-red light emitter that passes light through the breath sample.

7. A system for analyzing a breath sample comprising:
a carbon dioxide sensor configured to receive the breath sample and generate a sensor output indicating a carbon dioxide measurement in the breath sample;
a signal converter communicatively coupled to the carbon dioxide sensor via a data receiver, wherein the signal converter is configured to process the sensor output and output a digital signal;
a processor device communicatively coupled to the signal converter and a transducer, wherein the processor device is configured to:
  receive the digital signal;
  generate a periodic waveform based on the received digital signal, wherein the periodic waveform indicates a carbon dioxide concentration in the breath sample;
  analyze the periodic waveform to generate a dataset of the carbon dioxide concentration in the breath sample, wherein the dataset includes even harmonics and odd harmonics;
  detect an adverse respiratory event in the dataset by:
    determining that the even harmonics in the dataset are out of phase with the odd harmonics;
    identifying the adverse respiratory event based on the determining that the even harmonics in the dataset are out of phase with the odd harmonics; and
    generating a control signal directing the transducer to produce an audible alert signal that indicates the presence of the adverse respiratory event.

8. The system of claim 7, further comprising a pulse oximeter communicatively coupled to the processor device, wherein the pulse oximeter is configured to measure a level of oxygen saturation.

9. The system according to claim 7, wherein the carbon dioxide sensor comprises an infra-red light emitter that passes light through the breath sample.

10. A system for analyzing a breath sample comprising:
a carbon dioxide sensor configured to receive the breath sample and generate a sensor output indicating a carbon dioxide measurement in the breath sample;
a signal converter communicatively coupled to the carbon dioxide sensor via a data receiver, wherein the signal converter is configured to process the sensor output and output a digital signal;
a processor device communicatively coupled to the signal converter and a transducer, wherein the processor device is configured to:
  receive the digital signal;
  generate a periodic waveform based on the received digital signal, wherein the periodic waveform indicates a carbon dioxide concentration in the breath sample;
  analyze the periodic waveform to generate a dataset of the carbon dioxide concentration in the breath sample;
  detect an adverse respiratory event in the dataset by:
    obtaining a cumulative probability distribution of the periodic waveform;
    determining that a slope of the cumulative probability distribution of the periodic waveform is a negative slope;
    identifying the adverse respiratory event based on the determining that the slope of the cumulative probability distribution of the periodic waveform is a negative slope; and
    generating a control signal directing the transducer to produce an audible alert signal that indicates the presence of the adverse respiratory event.

11. The system of claim 10, further comprising a pulse oximeter communicatively coupled to the processor device, wherein the pulse oximeter is configured to measure a level of oxygen saturation.

12. The system according to claim 10, wherein the carbon dioxide sensor comprises an infra-red light emitter that passes light through the breath sample.

* * * * *